(12) United States Patent
Cowart et al.

(10) Patent No.: US 12,304,704 B2
(45) Date of Patent: *May 20, 2025

(54) STACKABLE EYE SHIELDS

(71) Applicant: DeRoyal Industries, Inc., Powell, TN (US)

(72) Inventors: Walter C. Cowart, Blaine, TN (US); Ethan Edward Valentine, Knoxville, TN (US); Nicholas John Poker, Knoxville, TN (US); Phillip David Peery, Sweetwater, TN (US)

(73) Assignee: DeRoyal Industries, Inc., Powell, TN (US)

( * ) Notice: Subject to any disclaimer, the term of this patent is extended or adjusted under 35 U.S.C. 154(b) by 470 days.

This patent is subject to a terminal disclaimer.

(21) Appl. No.: 17/477,805

(22) Filed: Sep. 17, 2021

(65) Prior Publication Data

US 2023/0091444 A1 Mar. 23, 2023

(51) Int. Cl.
*G02C 5/00* (2006.01)
*A41D 13/11* (2006.01)
(Continued)

(52) U.S. Cl.
CPC ........ *B65D 5/0245* (2013.01); *A41D 13/1184* (2013.01); *B65D 85/62* (2013.01);
(Continued)

(58) Field of Classification Search
CPC .......... G02C 5/001; G02C 5/008; G02C 1/10; G02C 1/04; G02C 1/02; A61F 9/02;
(Continued)

(56) References Cited

U.S. PATENT DOCUMENTS

| 653,086 A | 7/1900 | Houts |
| 1,860,324 A | 5/1932 | Einson |

(Continued)

FOREIGN PATENT DOCUMENTS

| EP | 2305190 A1 * | 4/2011 | ............ A61F 9/025 |
| GB | 1210962 A | 11/1970 | |
| GB | 2442755 A | 4/2008 | |

OTHER PUBLICATIONS

DeRoyal Inc, Facial Protection Products Catalog, Reprint # 0-1606, Rev. 12/20, (6 pages). www.deroyal.com, Powell, Tennessee Dec. 2020.

(Continued)

*Primary Examiner* — Wyatt A Stoffa
*Assistant Examiner* — Samanvitha Sridhar
(74) *Attorney, Agent, or Firm* — Luedeka Neely, P.C.

(57) ABSTRACT

A container having a stack of eye shields, includes a stack of eye shields having a plurality of eye shields stacked one on top of another. The stack of eye shields is in a sloped configuration in which ear pieces of frames of the eye shields are generally aligned with one another and disposed at an angle relative to horizontal of from about 10 to about 35 degrees. A container is provided having a horizontal bottom onto which the stack of eye shields is supported, the container having a top opposite the bottom, the top being sloped to be substantially parallel to the ear pieces of the eye shields of the stack of eye shields.

7 Claims, 15 Drawing Sheets

(51) Int. Cl.
 *B65D 5/02* (2006.01)
 *B65D 85/62* (2006.01)
 *G02C 1/02* (2006.01)

(52) U.S. Cl.
 CPC ............... *G02C 1/02* (2013.01); *G02C 5/001* (2013.01); *G02C 5/008* (2013.01)

(58) Field of Classification Search
 CPC ........ B65D 5/0245; B65D 5/029; B65D 5/16; B65D 5/542; B65D 5/0254
 USPC ............................ 351/103, 110; 2/12, 13, 15
 See application file for complete search history.

(56) References Cited

U.S. PATENT DOCUMENTS

| | | | |
|---|---|---|---|
| 2,006,445 A | | 7/1935 | Davidson |
| 2,030,996 A | | 2/1936 | Lustig |
| 2,031,575 A | | 2/1936 | Roe |
| 2,137,906 A | | 11/1938 | Cummings |
| 2,517,030 A | | 8/1950 | Ringler |
| 3,180,561 A | | 4/1965 | Hanns-Dieter |
| 4,822,158 A | | 4/1989 | Porsche |
| 4,843,643 A | * | 7/1989 | Parissenti .......... A41D 13/1161 351/158 |
| 5,375,702 A | | 12/1994 | Fiallo |
| 5,692,522 A | * | 12/1997 | Landis ...................... A61F 9/02 128/857 |
| 5,768,716 A | * | 6/1998 | Porsche ................. G02C 5/143 2/454 |
| 5,862,530 A | * | 1/1999 | Shillington ............. A61F 9/025 2/427 |
| 6,533,412 B1 | | 3/2003 | Wang et al. |
| 6,964,067 B1 | | 11/2005 | Hartman |
| 7,011,404 B2 | * | 3/2006 | Howard ................... G02C 1/04 351/86 |
| 7,661,815 B2 | | 2/2010 | Lipawsky |
| 8,458,813 B2 | * | 6/2013 | Grad ........................ A42B 3/20 2/13 |
| 8,992,007 B2 | | 3/2015 | Li |
| 9,546,031 B2 | * | 1/2017 | Healy ................ B65D 77/0413 |
| 10,517,763 B2 | | 12/2019 | Quinn et al. |
| 10,543,955 B1 | * | 1/2020 | Turturro ................ B65D 5/724 |
| 10,702,345 B2 | * | 7/2020 | Saito ........................ G02C 7/12 |
| 11,427,378 B2 | * | 8/2022 | Schultz ................ B65D 5/4204 |
| 2008/0087556 A1 | | 4/2008 | Henke et al. |
| 2009/0314661 A1 | | 12/2009 | Fisher et al. |
| 2015/0351965 A1 | * | 12/2015 | Umentum ................. A47F 1/08 2/427 |
| 2017/0239089 A1 | | 8/2017 | Quinn et al. |
| 2021/0253299 A1 | | 8/2021 | Dean et al. |

OTHER PUBLICATIONS

DeRoyal Inc, Facial Protection Products, Reprint # 0-1606, www.deroyal.com, (2 pages), Powell, Tennessee Dec. 2020.

Katharina Gabrich, European Patent Office, Munich Germany, EP 22 19 5385, Communication, European Search Report and Annex to the European Search Report, dated Dec. 15, 2022, place of search Munich, search completed on Dec. 6, 2022, 5 pages.

\* cited by examiner

STACKABLE EYE SHIELDS

FIELD

The present disclosure relates to eye shields. More particularly, the disclosure relates to improved molded eye shield structures configured to be stackable in a container for shipping and dispensing of the stack of eye shields.

BACKGROUND

Improvement is desired in the manufacture of disposable eye shields of the type having a molded plastic frame with ear pieces and a lens that is secured to the frame to provide an eye shield.

One need in the prior art is for eye shields that can easily be stacked one on top of another for shipping and dispensing and that tend to remain parallel to one another in the stacked orientation. Conventional eye shields are provided in stacks in boxes, but the eye shields become entangled and shifted and become difficult to dispense without a user handling several of the eye shields at a time.

The present disclosure advantageously provides eye shields that are aesthetically pleasing and configured to facilitate stacking of the eye shields so that the eye shields remain aligned and parallel to one another and do not entangle so that a user can just grasp the top most eye shield from the stack and not have to handle underlying ones.

Also provided in the disclosure is a container that aesthetically and structurally compliments the stacked eye shields and facilitates shipping and dispensing of the eye shields.

SUMMARY

The above and other needs are met by an improved eye shield configured to be provided in a stack of like eye shields for shipping and dispensing.

In one aspect, a stack of eye shields according to the disclosure includes a plurality of eye shields, each eye shield having: a frame having a plurality of spaced apart elevated support surfaces along and rising above an upper portion of the frame; and a lens installed on the frame.

The plurality of eye shields is provided in a stack having the plurality of eye shields being stacked one on top of another with each of the eye shields oriented substantially parallel to one another with each of the elevated surfaces of an overlying one of the frames of the stack being slightly forward of a corresponding one of the elevated surfaces of the underlying frame of the stack, with each frame of each eye shield of the stack having a gap therebetween except at contact surfaces where the elevated support surfaces contact an adjacent lower surface of an overlying eye shield. The elevated support surfaces of the frames stabilize the stack of the eye shields for shipping and dispensing of the stack of the eye shields.

In another aspect, a container and stack of eye shields contained therein for shipping and dispensing of the eye shields according to the disclosure includes a plurality of eye shields, each eye shield having: a frame having a plurality of spaced apart elevated support surfaces along and rising above an upper portion of the frame; and a lens installed on the frame.

A stack of the plurality of eye shields, includes the eye shields being stacked one on top of another with each of the eye shields oriented substantially parallel to one another with each of the elevated surfaces of an overlying one of the frames of the stack being slightly forward of a corresponding one of the elevated surfaces of the underlying frame of the stack, with each frame of each eye shield of the stack having a gap therebetween except at contact surfaces where the elevated support surfaces contact an adjacent lower surface of an overlying eye shield, with the elevated support surfaces of the frames stabilizing the stack of the eye shields.

A container is provided into which the stack of eye shields is received for shipping and dispensing. The container has a top sloped to be substantially parallel to the ear pieces of the eye shields of the stack of eye shields.

In a further aspect, container having a stack of eye shields according to the disclosure, includes a stack of eye shields having a plurality of eye shields stacked one on top of another. The stack of eye shields is in a sloped configuration in which ear pieces of frames of the eye shields are generally aligned with one another and disposed at an angle relative to horizontal of from about 10 to about 35 degrees. A container is provided having a horizontal bottom onto which the stack of eye shields is supported, the container having a top opposite the bottom, the top being sloped to be substantially parallel to the ear pieces of the eye shields of the stack of eye shields.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
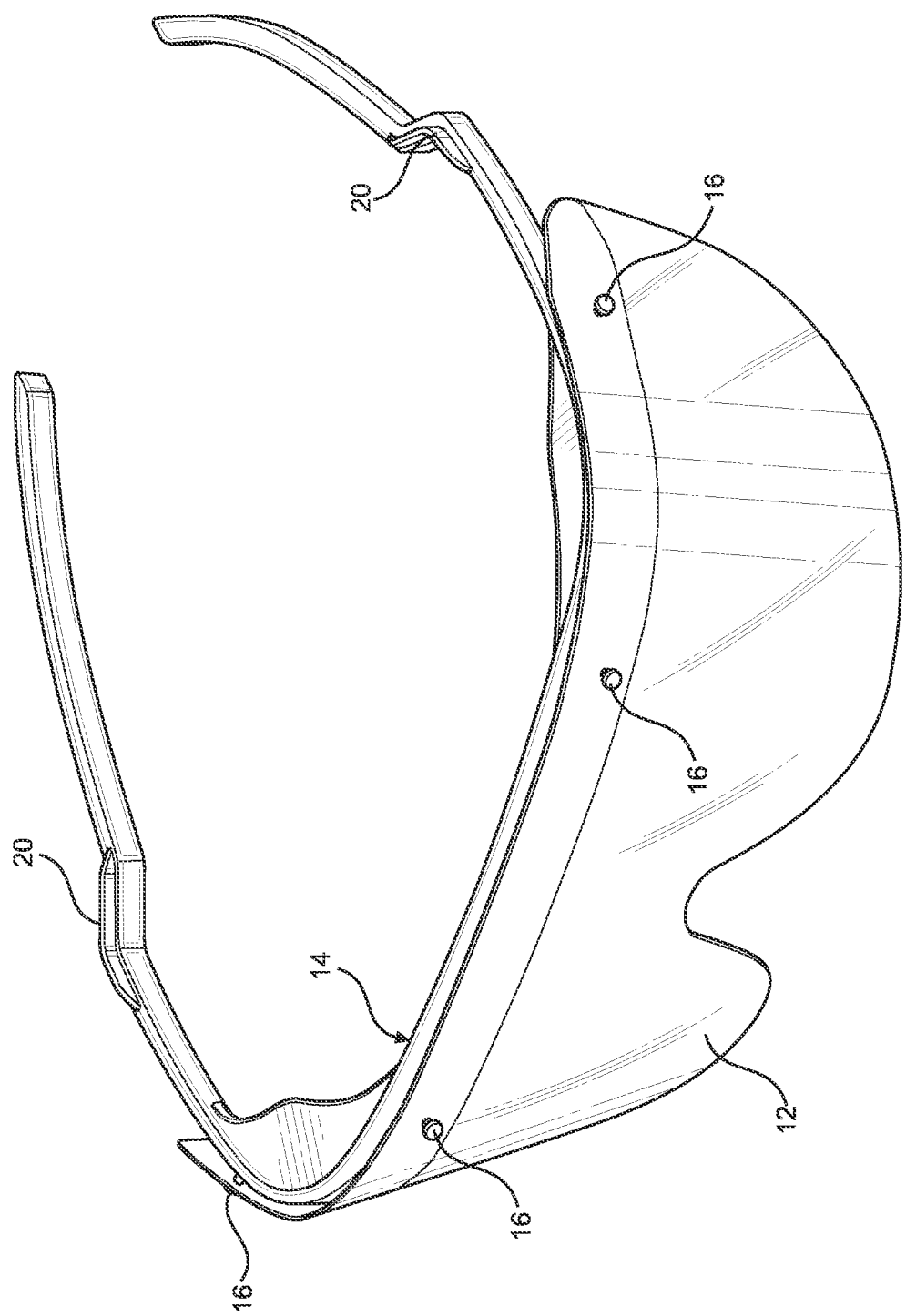
FIG. 1 is a perspective view of an eye shield according to the disclosure and FIG. 2 is an exploded view thereof.
Figure 2:
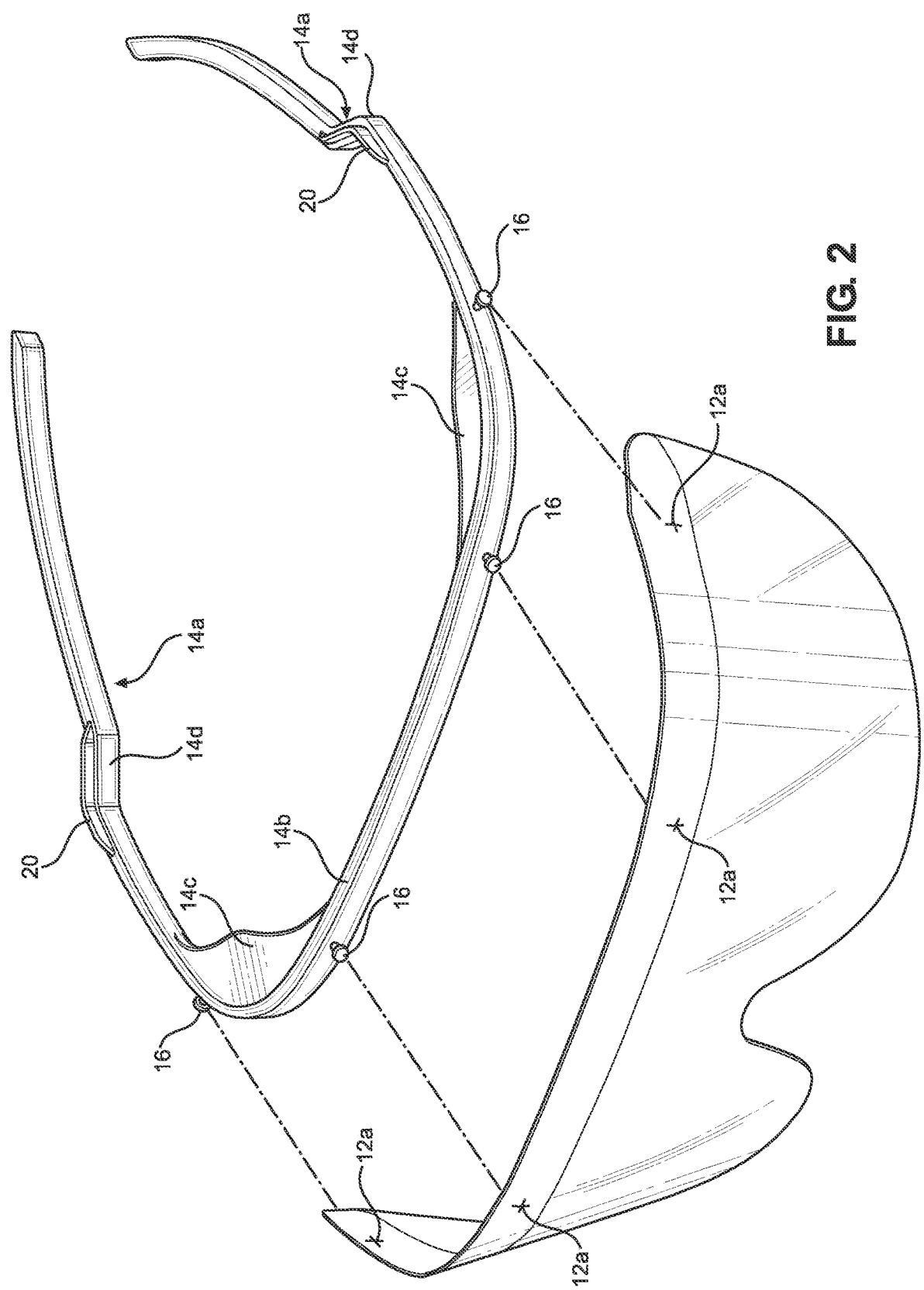
Figure 3:
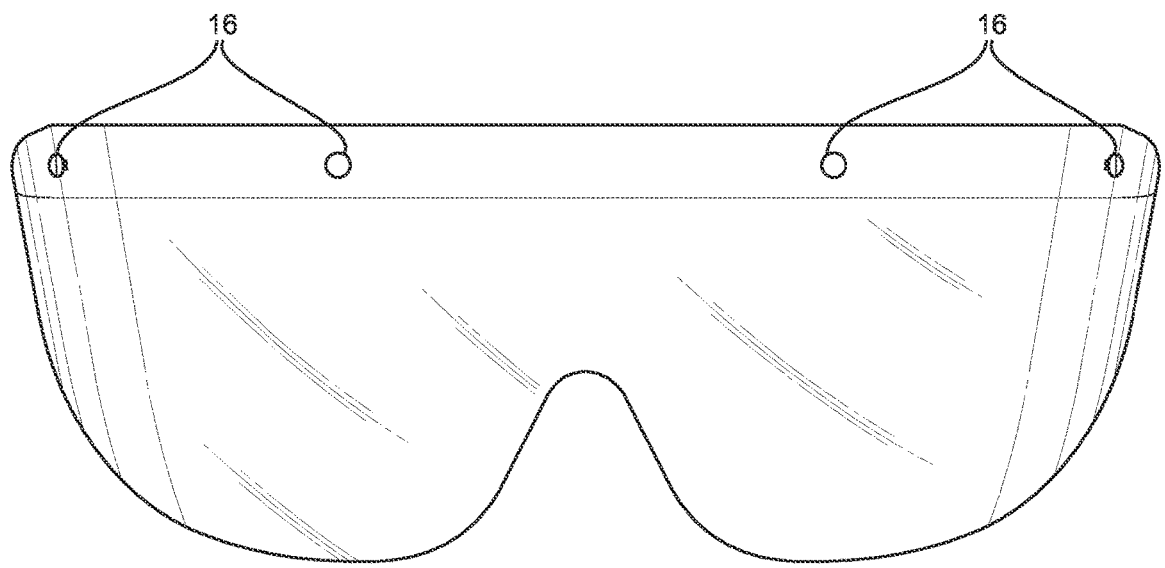
FIG. 3 is a frontal view thereof.

With reference to the drawings, the disclosure provides an eye shield 10. The eye shields 10 are desirably configured to facilitate vertical stacking of the eye shields 10 so that the eye shields 10 do not entangle so that a user can just grasp the top most eye shield from the stack and not have to handle underlying ones. The appearance of the eye shields 10 is also configured to be aesthetically pleasing and includes various ornamental aspects and features.

The eye shield 10 has a lens 12 attached in a releasable snap-fit relationship to a frame 14 by studs 16 formed on and projecting outwardly from the front of the frame 14.

The lens 12 is preferably a one-piece plastic lens die cut from flat plastic film or other suitable lens material. The lens 12 includes a plurality of spaced apart lens apertures 12a defined adjacent an upper edge of the lens 12. The apertures 12a are arranged to overlie the studs 16 and the apertures 12a may be configured as x-shaped cuts so as to frictionally engage the studs 16.

The frame 14 is preferably of molded plastic construction and has ear pieces 14a and a curved brow piece 14b. The brow piece 14b preferably has reduced material so as to flex for good fit, but may include corner braces 14c or other reinforcing or stiffening structures to maintain desired rigidity. The ear pieces 14a meet the brow piece 14b at junctures 14d that are desirably non-linear and angle the ear pieces 14a inwardly.

The brow piece 14b also includes the studs 16. The studs 16 have an enlarged head that is pushed through the apertures 12a.

The frame 14 also includes a plurality of elongate, narrow elevated members or ridges 20 defined along upper surfaces of the ear pieces 14a of the frame 14. As described in more detail below, the ridges 20 of the frames 14 cooperate to facilitate vertical stacking of the eye shields 10 and enable maintenance of the stacked eye shields 10 in a vertically stacked and substantially parallel relationship for shipping and dispensing of the eye shields 10 in the stacked relationship.

Figure 13:
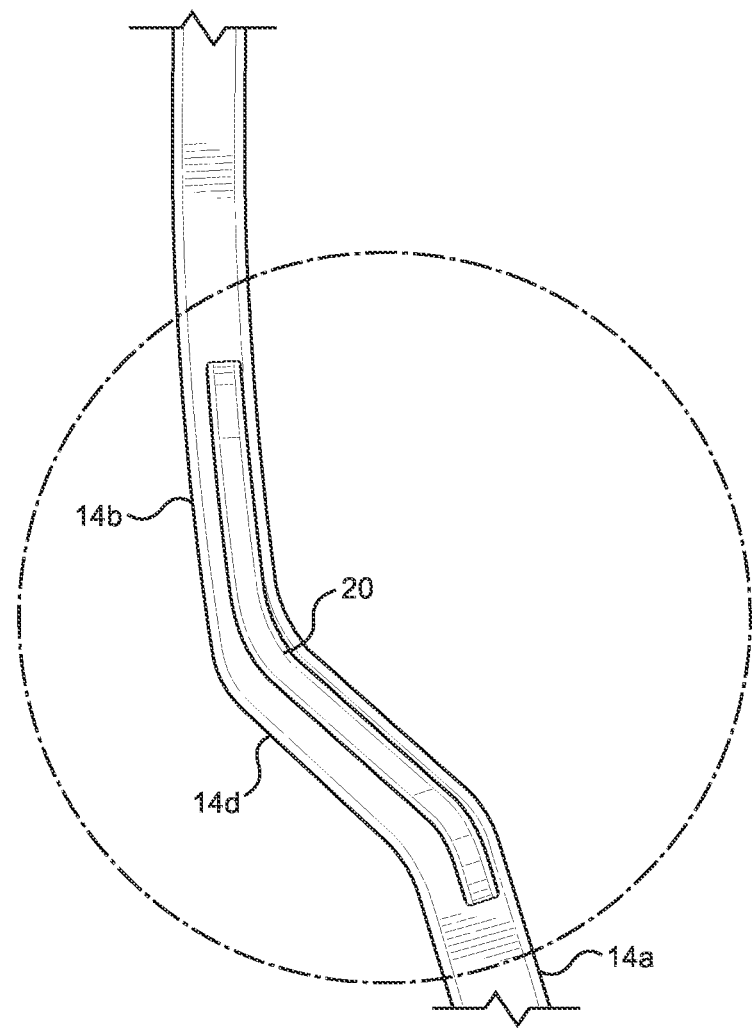
FIGS. 13-14 depict stacking ridges of the eye shields.
Figure 14:
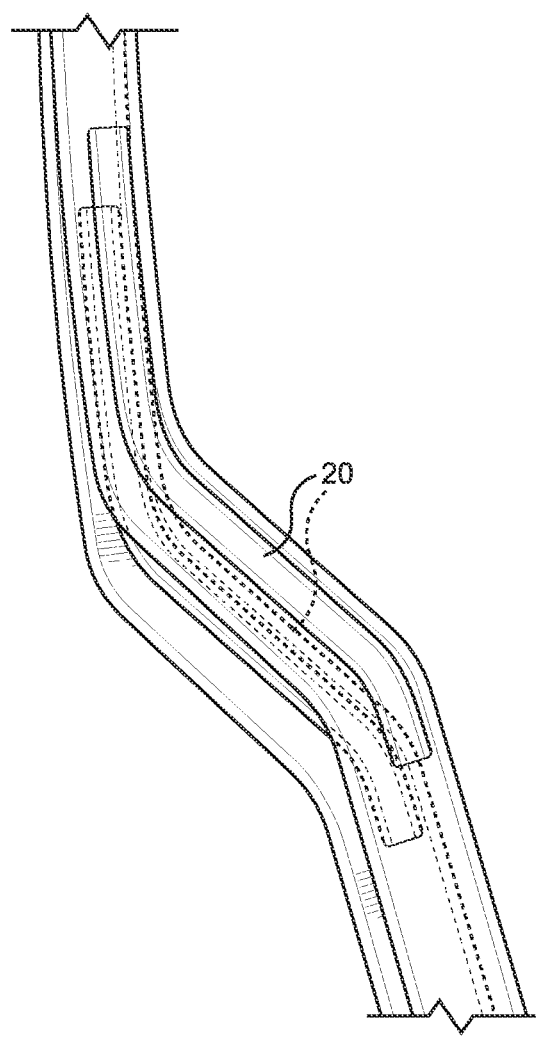

With reference to FIGS. 13-14, the ridges 20 are defined on an upper surface of the frame 14 at the non-linear juncture 14d of each ear piece 14a to the brow piece 14b, so as to span along a portion of the ear piece 14a, the brow piece 14b and the juncture 14d. The ridges 20 are elongate, narrow ridges that define a crooked raised line along the top of the frame 14. The manner of stacking of the ridges 20 also inhibits the eye shields 10 in the stack from shifting and becoming entangled so that a user can just grasp the top most eye shield from the stack to remove it from the stack and not have to handle underlying ones.

Figure 4:
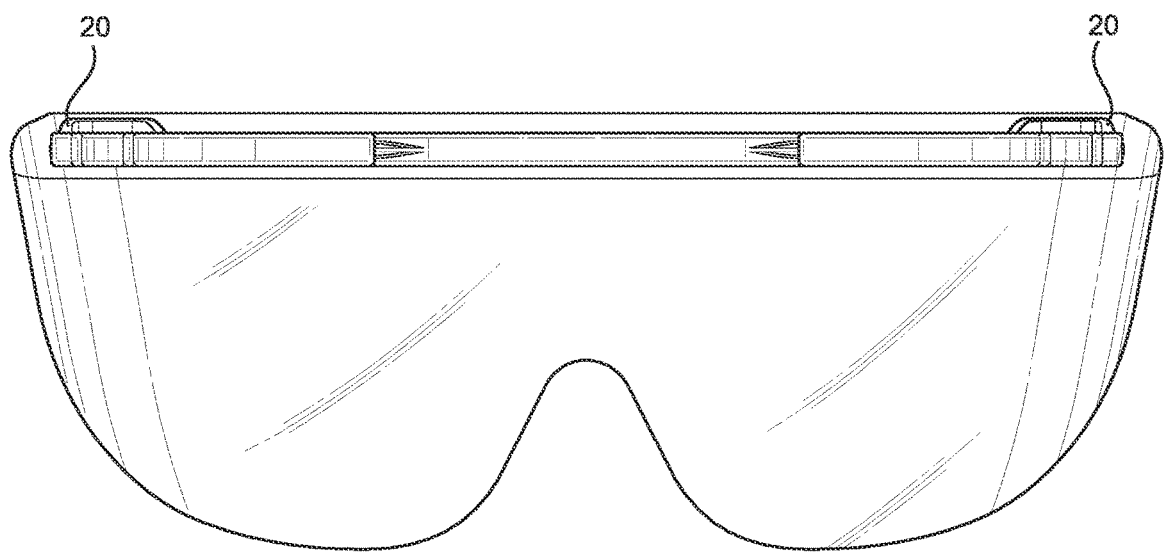
FIG. 4 is a rear view thereof.
Figure 5:
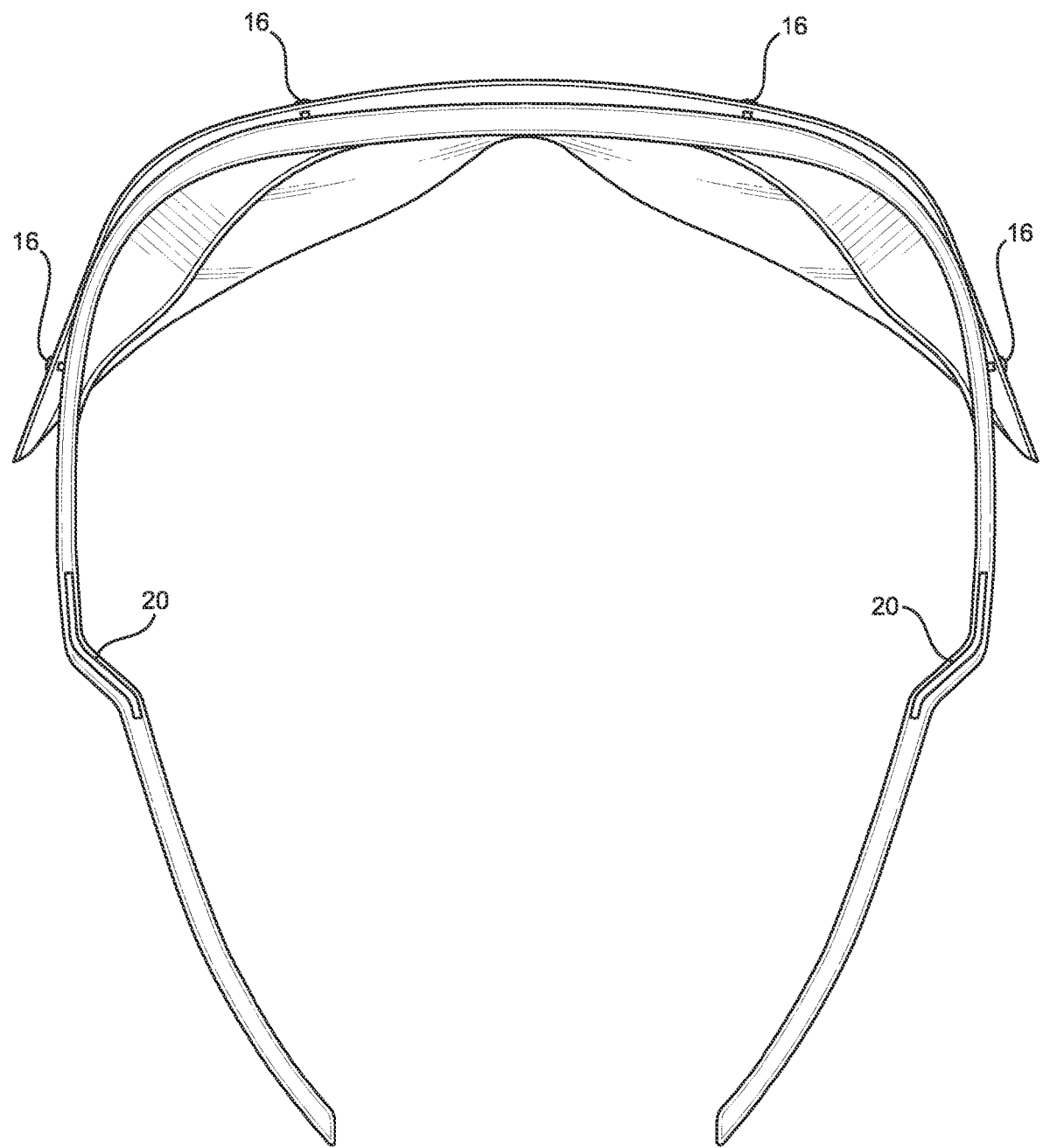
FIG. 5 is a top view thereof.
Figure 6:
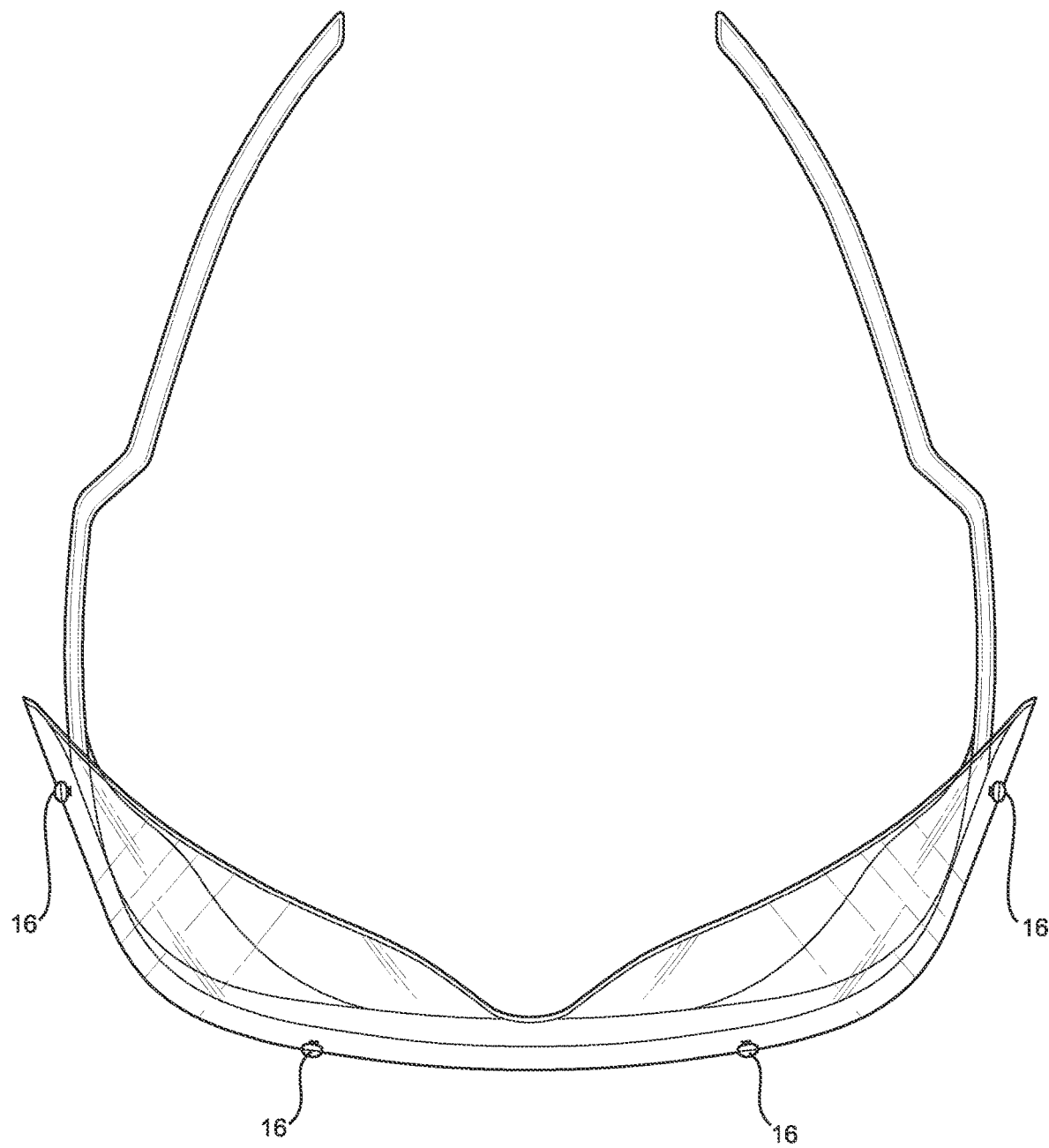
FIG. 6 is a bottom view thereof.
Figure 7:
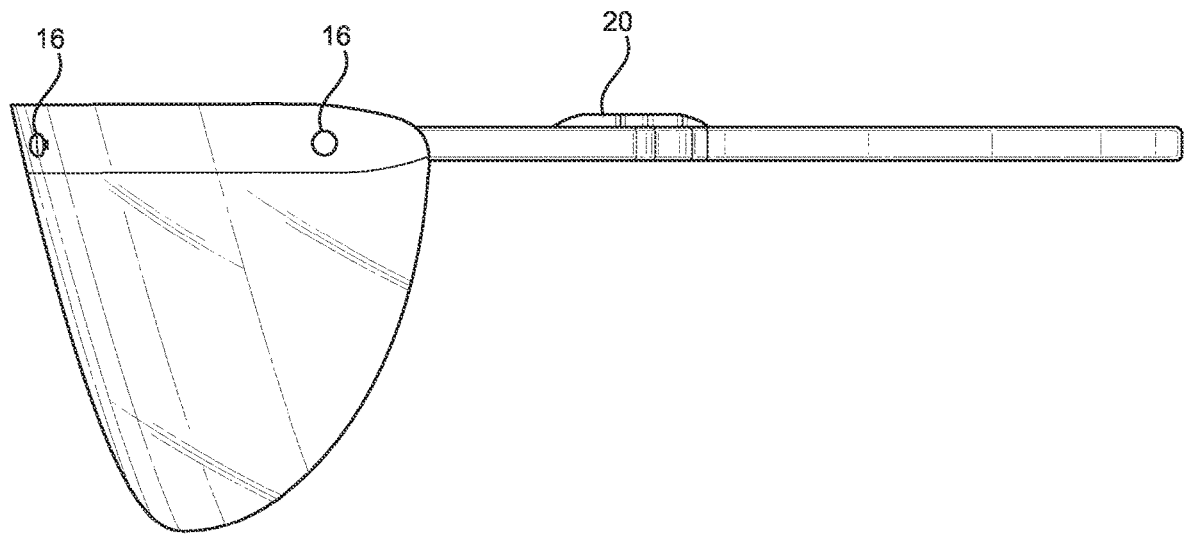
FIG. 7 is a left-side view thereof.
Figure 8:
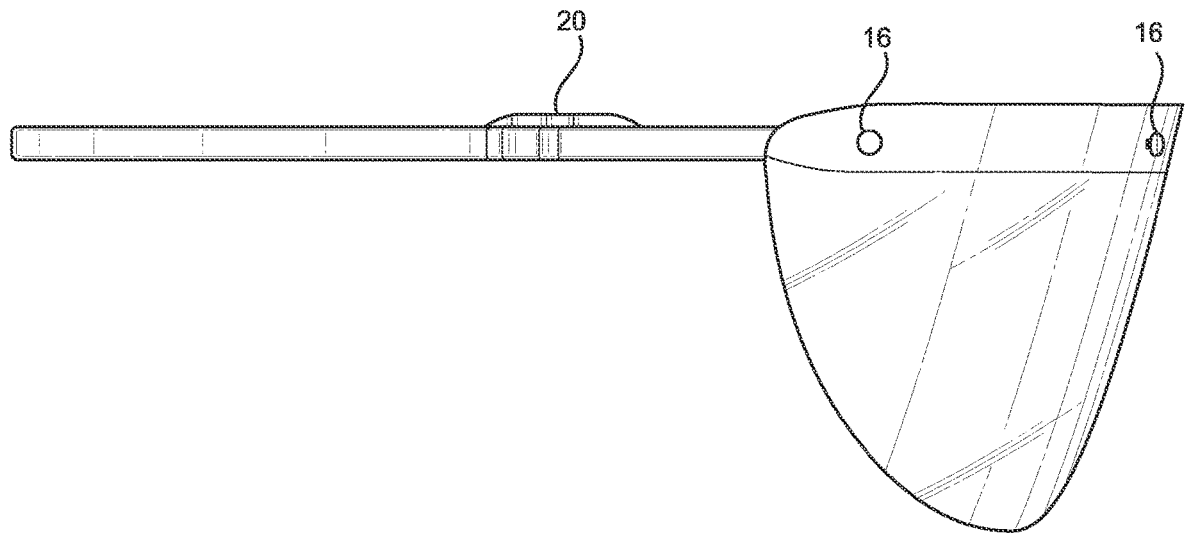
FIG. 8 is a right-side view thereof.
Figure 9:
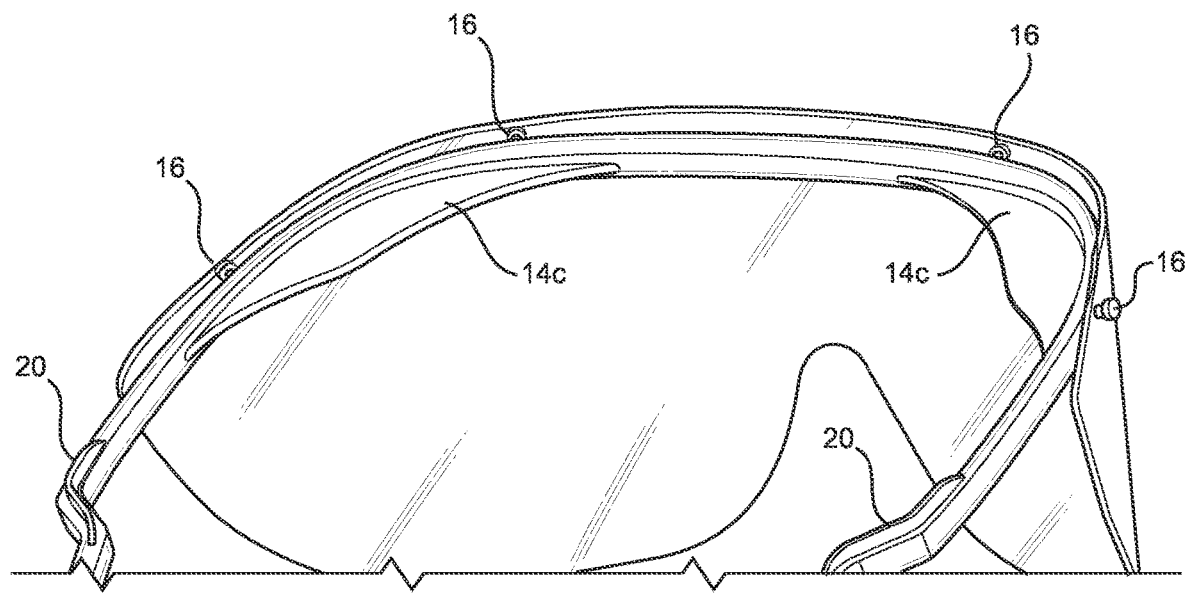
FIG. 9-10 show the frames of the eye shields.
Figure 10:
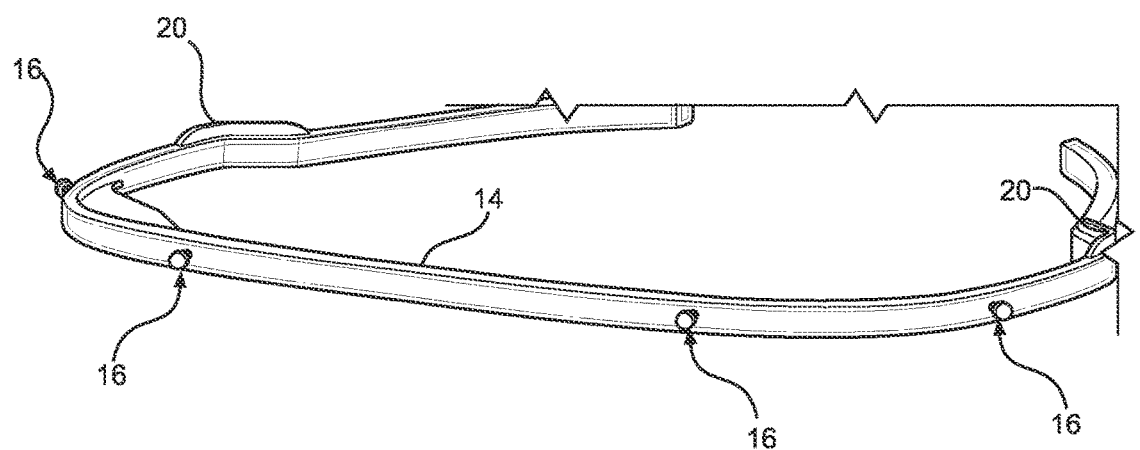
Figure 11:
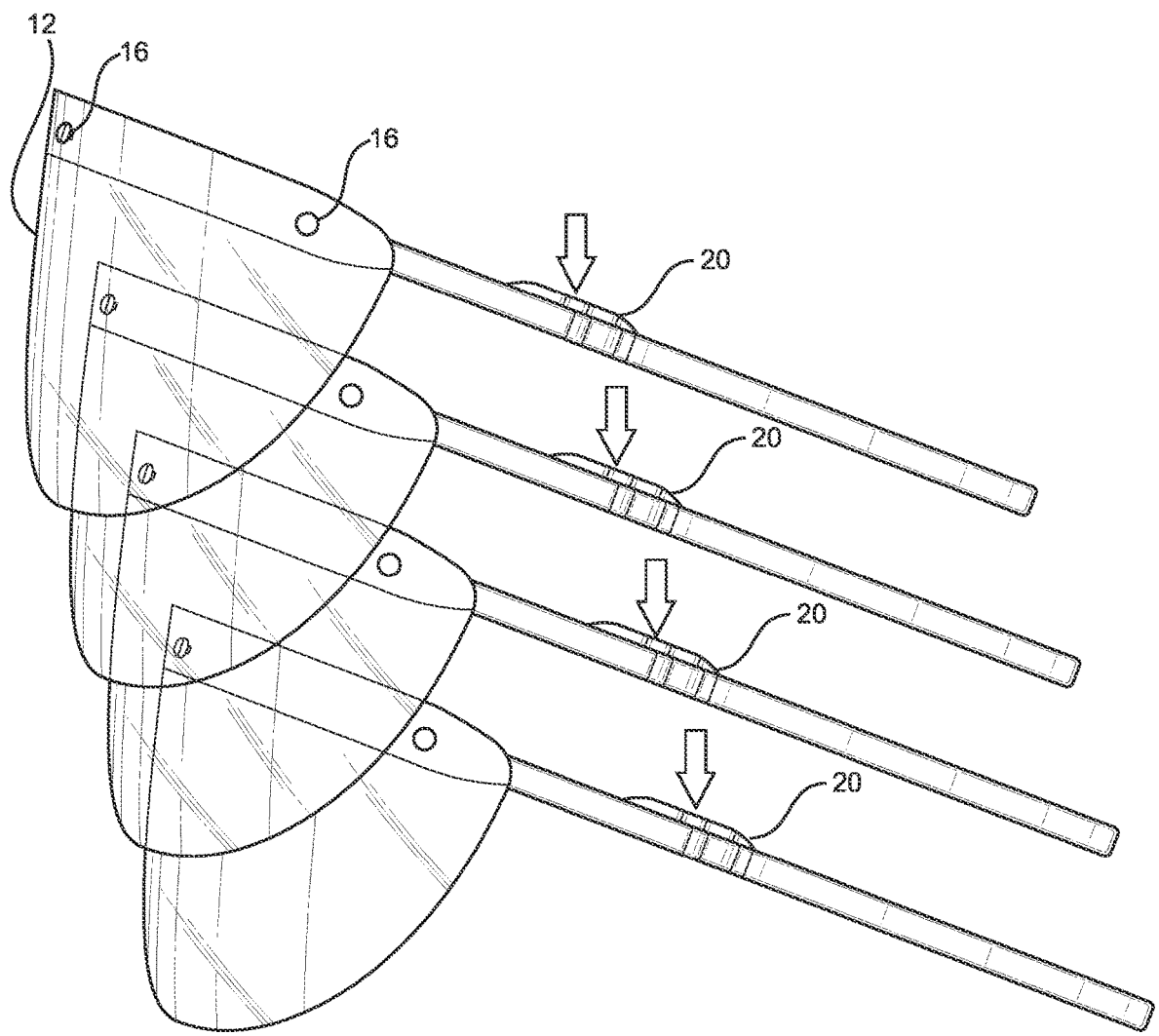
FIGS. 11-12 depict stacking of the eye shields.
Figure 12:
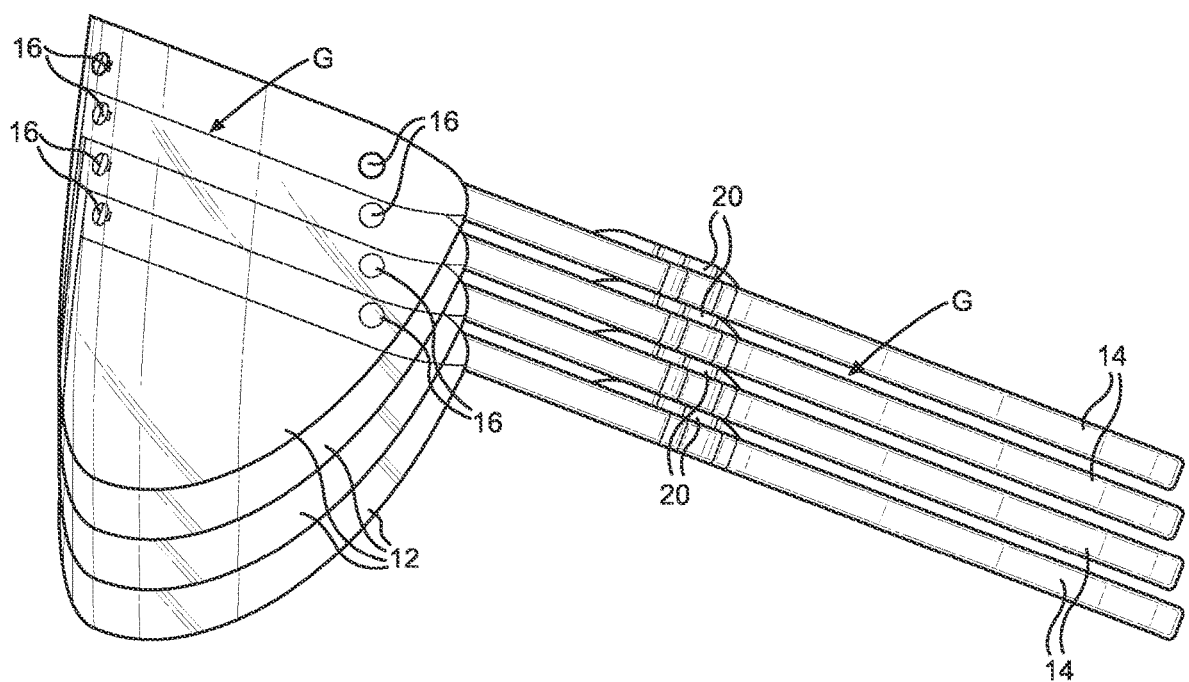

As shown in FIG. 4, the uppermost surfaces of the ridges 20 all lie in a common plane elevated above the frame 14. As such, the ridges 20 of adjacent ones of the eye shields 10 in a stack are contact surfaces between the stacked eye shields 10.

As a result, each frame 14 of each eye shield 10 of the stack has a gap G therebetween except at the elevated contact surfaces provided by the ridges 20 of the lower eye shield which contact and support the lower surface of the frame 14 of the overlying eye shield 10, as shown in FIGS. 12-15. Thus, the elevated contact surfaces provided by the ridges 20 of the frames 14 stabilize the stack of the eye shields for shipping and dispensing of the stack of the eye shields.

As depicted in FIGS. 11-12 and 14-15, in stacking of the eye shields 10, the stack is substantially vertical and the eye shields 10 are aligned to be substantially parallel in a stack, but do not directly vertically stack. This is because of the thickness of the lenses 12 and that each upper lens 12 in a stack overlaps the underlying lens 12. As such, each upper ridge 20 in the stack is slightly forward of the underlying ridge 20.

Providing the ridges 20 at the temple locations of the frame 14 enables weight loading of the eye shields to be at locations away from or remote from the lenses 12 to avoid stresses to the lenses 12 from stacking of the eye shields 10. Thus, the ridges 20 provide the primary weight bearing locations for the stack of eye shields.

Figure 15:
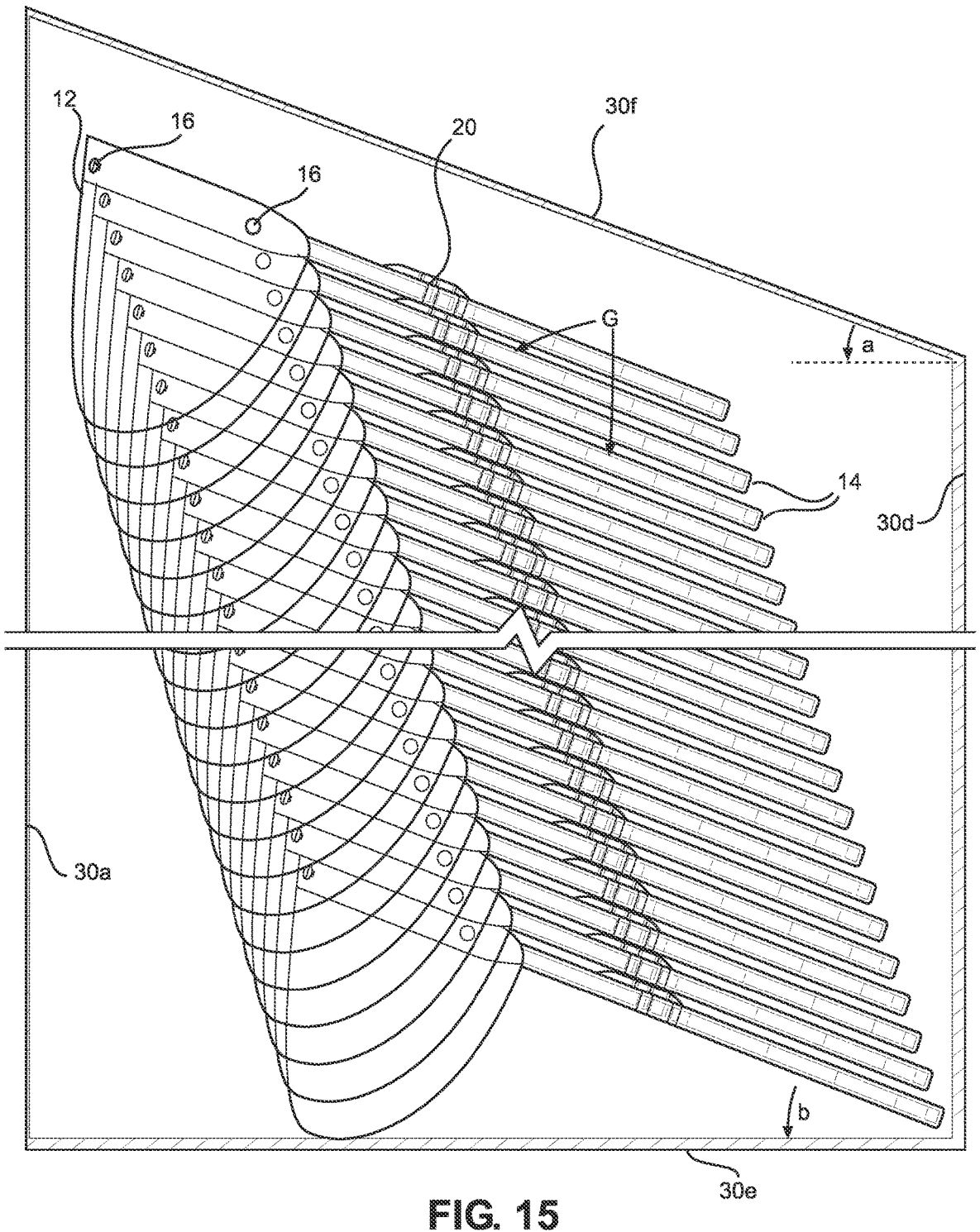
FIG. 15 shows the eye shields stacked for shipping and display in a specially configured container suitable for shipping and dispensing of the eye shields.
Figure 16:
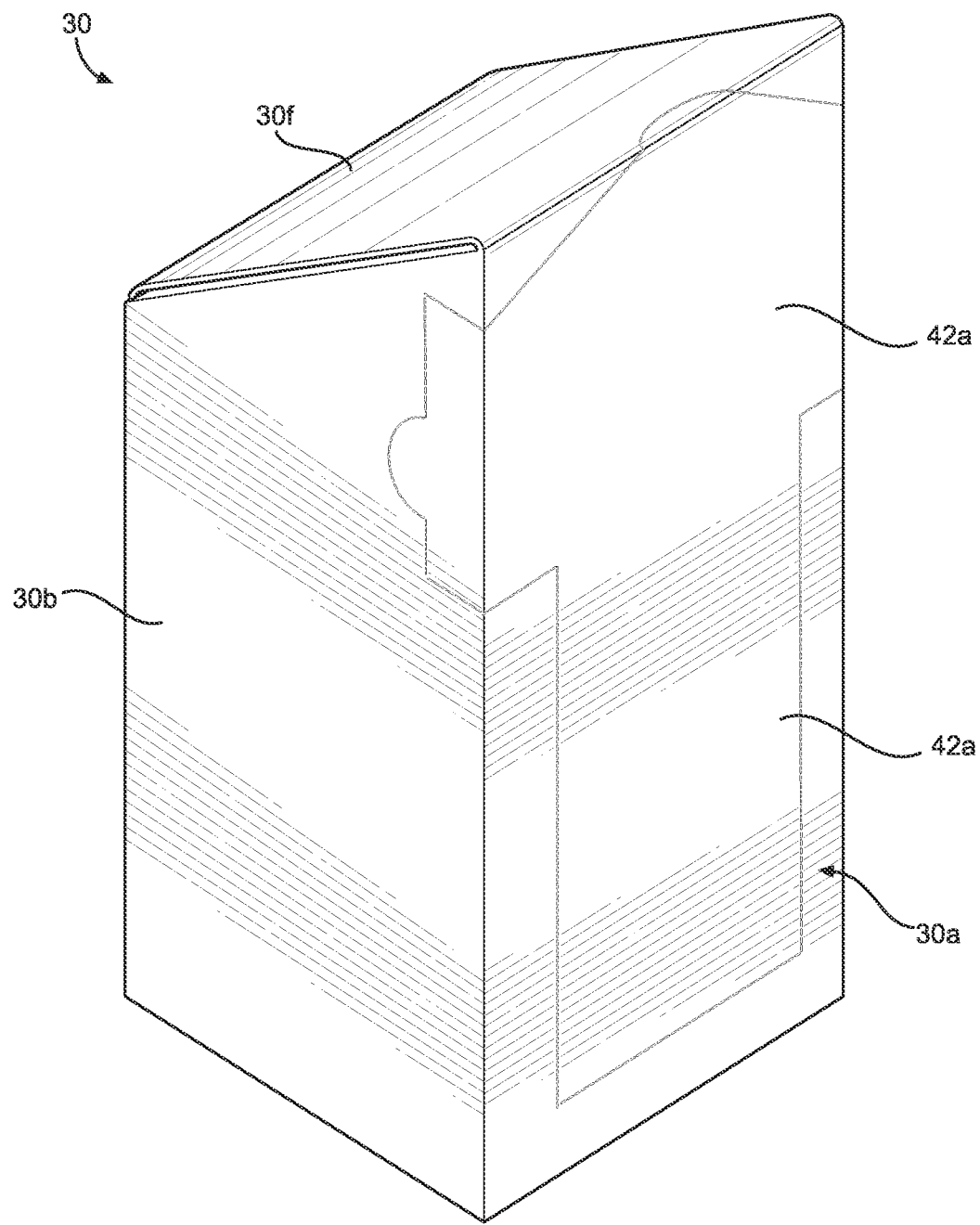
FIG. 16 shows the container configured for shipping of the eye shields.
Figure 17:
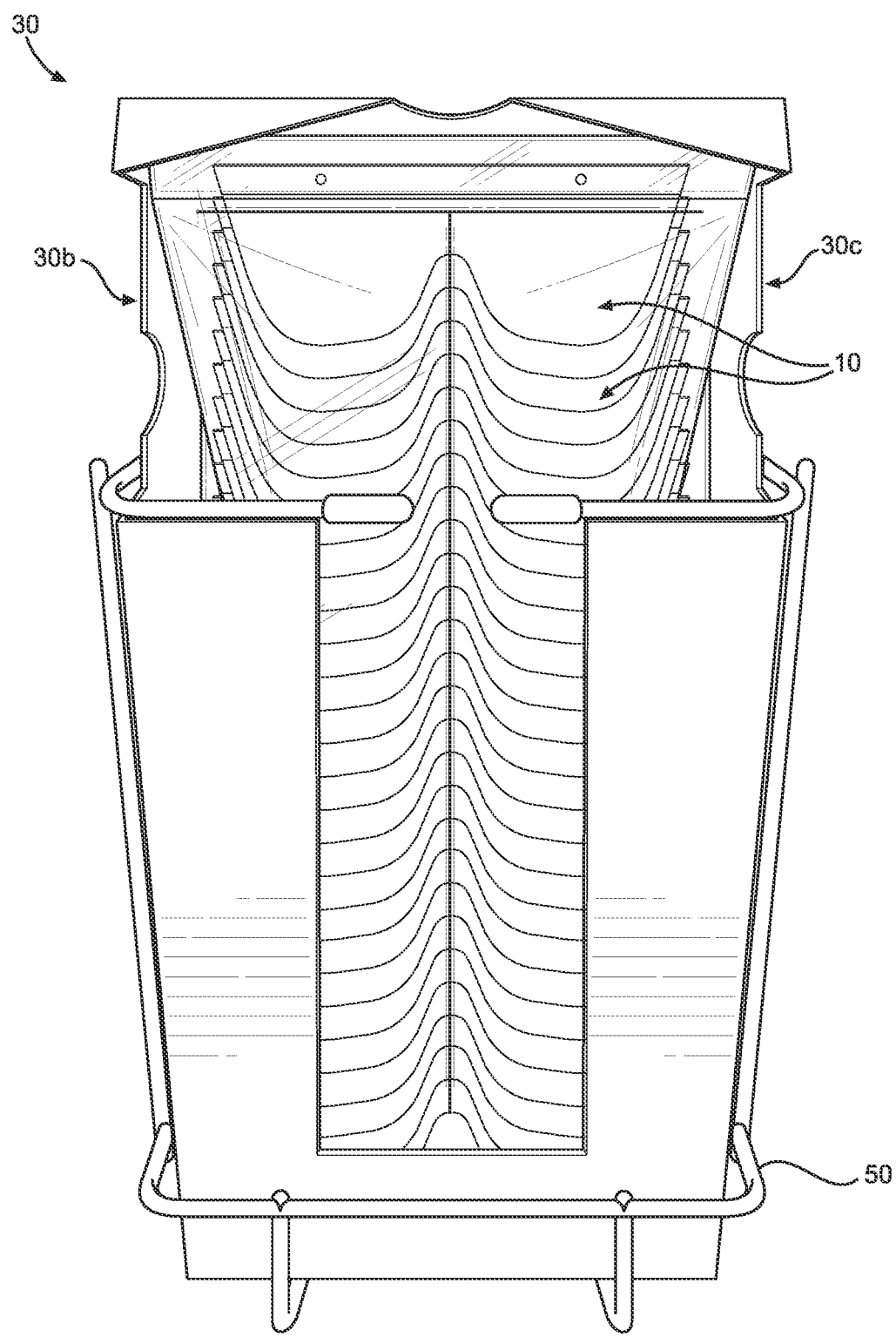
FIG. 17 shows the container configured for dispensing of the eye shields.

With reference now to FIGS. 15-17, there is shown a dispensing container 30 for the stacked eye shields 10. The dispensing container 30 is desirably configured for storing and shipment of the eye shields 10 in a stacked configuration as shown in FIG. 15, and for dispensing of the eye shields 10 to users of the eye shields, as shown in FIG. 17. The dispensing container 30 is also configured to be aesthetically pleasing and includes various ornamental aspects and features. The container 30 is also configured to facilitate the stacked eye shields and the dispensing of the of the eye shields in a manner such that a user can just grasp the top most eye shield 10 from the stack to remove it from the stack and not have to handle underlying ones.

The erected container includes a front 30a, sides 30b and 30c, rear 30d, bottom 30e, and top 30f. The front 30a, sides 30b and 30c, and rear 30d are vertical surfaces perpendicular to the bottom 30e and rise upwardly from bottom 30e, which is horizontal. The top 30f slopes downwardly from the front 30a to the rear 30d and is disposed at an angle a relative to horizontal of from about 10 to about 35 degrees, most preferably from about 20 to 25 degrees.

As shown in FIG. 15, the eye shields 10 are substantially aligned to be substantially parallel to one another in the stack and are stacked in a sloped configuration in which the ear pieces 14 are generally aligned with one another and disposed at an angle b relative to the horizontal bottom 30e of from about 10 to about 35 degrees, most preferably from about 20 to 25 degrees. Thus, the top 30f is desirably sloped to be substantially parallel to the generally uniformly sloped ear pieces 14 of the stacked eye shields 10.

It has been observed that the stacking features of the eye shields 10 tend to prevent at least the bulk of the eye shields from shifting and becoming entangled in the stack. That is, while a minor few of the eye shields could potentially shift a little from the stacked orientation as shown, it has been observed that the bulk of the eye shields do not shift and the stack does not become entangled such that a user can just grasp the top most eye shield from the stack to remove it from the stack and not have to handle underlying ones.

Figure 18:
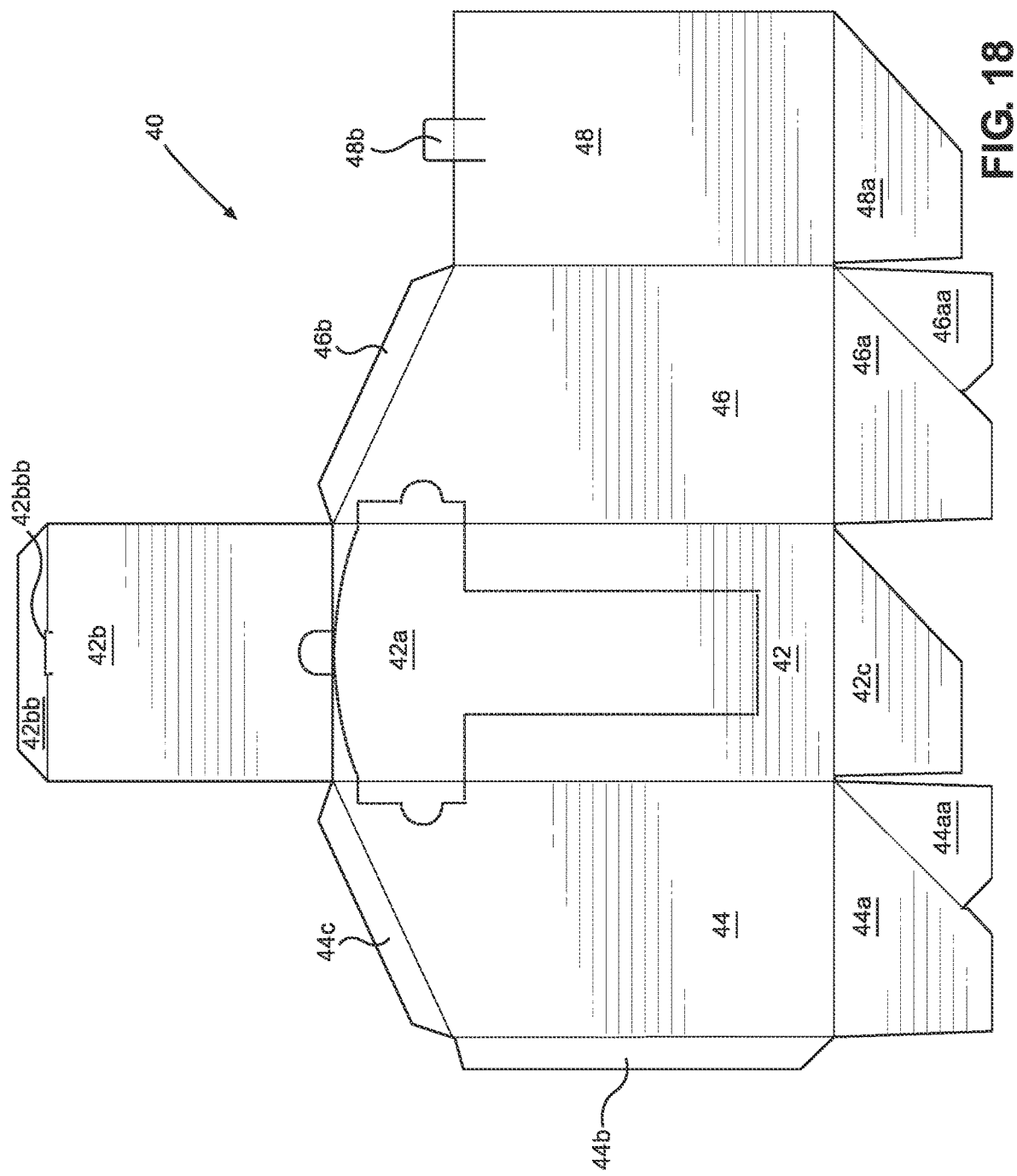
FIG. 18 shows a blank for making the container.

The dispensing container 30 may be of paperboard construction and formed of a one-piece blank 40, as shown in FIG. 18. The dispensing container 30 may be hung from a wall or the like, and may be supported by a wire hanger 50 that can be attached to a wall (FIG. 17).

Returning to FIG. 18, the blank 40 includes a front panel 42, opposite side panels 44 and 46 foldable relative to the front panel 42, and rear panel 48 foldable relative to the side panel 46.

The front panel 42 includes a tear-away section 42a having a border formed by perforations and configured to be removed to enable access to the stacked eye shields 10, a foldable top flap 42b, a foldable bottom panel 42c, and a folding edge 42bb extending from the top flap 42b, with a slot 42bbb formed along the edge 42bb. The tear-away section 42 is generally T-shaped and includes portions that extend into the top flap 42b and the side panels 44 and 46 to facilitate access of the fingers of a user into the container 30 for removing the eye shields 10, generally one at a time, from the stack of eye shields in the container 30.

The side panel 44 includes a bottom flap 44a having a folding edge 44aa, a side flap 44b, and an upper flap 44c. The side panel 46 includes a bottom flap 46a having a folding edge 46aa, and an upper flap 46b. The rear panel 48 is includes a bottom flap 48a and an upper folding tab 48b configured to engage the slot 42bbb.

As will be appreciated, the disclosure advantageously provides eye shields configured to facilitate stacking of the eye shields so that the eye shields remain aligned and parallel to one another and do not entangle so that a user can just grasp the top most eye shield from the stack and not have to handle underlying ones.

A container that compliments the stacked eye shields is also provided which facilitates shipping and dispensing of the eye shields.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A stack of eye shields, comprising
a plurality of eye shields, each eye shield having:
   a frame having a curved brow piece and a pair of ear pieces extending rearwardly from opposite ends of the curved brow piece with an elevated support surface rising from an upper surface of each of the ear pieces of the frame and rearwardly spaced away from the curved brow piece; and
   a lens installed on the curved brow piece;
   wherein the plurality of eye shields is provided in a stack one on top of another while being oriented substantially parallel to one another; and the elevated support surfaces of an overlying frame of the stack is slightly in front of the elevated support surfaces of an underlying frame of the stack, with each frame of each eye shield of the stack having a gap therebetween except at contact surfaces, with the elevated support surfaces of the frames stabilizing the stack of eye shields.

2. The stack of eye shields of claim 1, wherein the elevated support surfaces comprise elongate ridges that define crooked raised lines.

3. The stack of eye shields of claim 1, wherein the elevated support surfaces are located at temple locations of the ear pieces of the frame.

4. The stack of eye shields of claim 1, wherein the stack is in a sloped configuration in which the ear pieces of the frames of the eye shields are generally aligned with one another and disposed at an angle relative to a horizontal of from about 10 to about 35 degrees.

5. The stack of eye shields of claim 4, further comprising a container into which the stack of eye shields is received for shipping and dispensing, the container having a top sloped to be substantially parallel to the ear pieces of the stack of eye shields.

6. A container and stack of eye shields contained therein for shipping and dispensing of the eye shields, comprising:
   a plurality of eye shields, each eye shield having:
      a frame having a curved brow piece and a pair ear pieces extending rearwardly from opposite ends of the curved brow piece with an elevated support surface rising from an upper surface of each of the ear pieces of the frame and rearwardly spaced away from the curved brow piece; and
      a lens installed on the curved brow piece;
   a stack of the plurality of eye shields, the eye shields being stacked one on top of another while being oriented substantially parallel to one another and the elevated support surfaces of an overlying frame of the stack is slightly in front of the elevated support surfaces of an underlying frame of the stack, with each frame of each eye shield of the stack having a gap therebetween except at contact surfaces, with the elevated support surfaces of the frames stabilizing the stack of the eye shields; and
   a container into which the stack of eye shields is received for shipping and dispensing, the container having a top sloped to be substantially parallel to the ear pieces of the eye shields of the stack of eye shields.

7. A container having a stack of eye shields, comprising:
a stack of eye shields comprising a plurality of eye shields stacked one on top of another, wherein the stack of eye shields is in a sloped configuration in which ear pieces of frames of the eye shields are generally aligned with one another and disposed at an angle relative to a horizontal of from about 10 to about 35 degrees; and
a container having a horizontal bottom onto which the stack of eye shields is stacked, the container having a top opposite the bottom, the top being sloped to be substantially parallel to the ear pieces of the eye shields of the stack of eye shields, and a front vertical panel configured to provide access to the stack of eye shields and a rear vertical panel, the front and rear vertical panels each extending between the bottom and the top, the slope of the top being from the front vertical panel downward to the rear vertical panel.

* * * * *